(12) United States Patent
Defaix et al.

(10) Patent No.: US 11,832,633 B2
(45) Date of Patent: Dec. 5, 2023

(54) PROTEIN ISOLATE AND PROCESS FOR THE PRODUCTION THEREOF

(71) Applicants: AVRIL, Paris (FR); UNIVERSITE DE LORRAINE, Nancy (FR); CENTRE NATIONAL DE LA RECHERCHE SCIENTIFIQUE, Paris (FR)

(72) Inventors: Claire Defaix, Villers-lés-Nancy (FR); Romain Kapel, Saint Max (FR); Olivier Galet, Trégueux (FR)

(73) Assignees: AVRIL, Paris (FR); UNIVERSITE DE LORRAINE, Nancy (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 455 days.

(21) Appl. No.: 16/764,739

(22) PCT Filed: Nov. 14, 2018

(86) PCT No.: PCT/EP2018/081263
§ 371 (c)(1),
(2) Date: May 15, 2020

(87) PCT Pub. No.: WO2019/096862
PCT Pub. Date: May 23, 2019

(65) Prior Publication Data
US 2020/0397018 A1  Dec. 24, 2020

(30) Foreign Application Priority Data

Nov. 15, 2017 (EP) ...................... 17201967
Dec. 5, 2017 (EP) ...................... 17205565

(51) Int. Cl.
*A23J 1/14*   (2006.01)
*C07K 1/34*   (2006.01)
*C07K 14/76*  (2006.01)

(52) U.S. Cl.
CPC ............... *A23J 1/142* (2013.01); *A23J 1/148* (2013.01); *C07K 1/34* (2013.01); *C07K 14/76* (2013.01); *C12Y 301/03* (2013.01)

(58) Field of Classification Search
CPC ........ C12Y 301/03; C07K 14/76; C07K 1/34; A23J 1/148; A23J 1/142
(Continued)

(56) References Cited

U.S. PATENT DOCUMENTS

| 4,889,921 A | * | 12/1989 | Diosady | .................... A23J 1/14 |
| | | | | 426/656 |
| 2006/0193965 A1 | * | 8/2006 | Newkirk | ................ A23K 10/37 |
| | | | | 426/629 |

(Continued)

FOREIGN PATENT DOCUMENTS

CA   2893703 A1 * 7/2014 .............. A23J 1/006

OTHER PUBLICATIONS

Cheung et al., Effect of pH and NaCl on the Emulsifying Properties of a Napin Protein Isolate, Food Biophysics (2015) 10:30-38 ( Year: 2015).*

(Continued)

*Primary Examiner* — Brent T O'Hern
(74) *Attorney, Agent, or Firm* — ARENTFOX SCHIFF LLP

(57) ABSTRACT

A process for producing a protein isolate from an oilseed meal, and the isolate thus obtained, said isolate comprising proteins and an amount of 4 wt. % or less of phytic acid, said amount of phytic acid being by weight of proteins in said isolate. The process may comprise the following steps:

(Continued)

a) providing an oilseed meal;

b) mixing the oilseed meal with a first aqueous solvent to form a slurry at a pH ranging from 6 to 7.8, said slurry having a solid phase;

c) separating said solid phase from said slurry, d) mixing said separated solid phase with a second aqueous solvent at a pH ranging from 1 to 3.5, preferably from 2 to 3, to form a mixture said mixture having a liquid phase;

e) separating said liquid phase from said mixture formed in step d);

f) f1) mixing the separated liquid phase to a phytase at a temperature and a pH suitable for phytase activity to obtain a mixture having a liquid phase and a solid phase;

and/or f2) mixing the separated liquid to a salt, to obtain a resulting liquid composition having a molar concentration of said salt ranging from 0.05M to 0.5M, at a temperature ranging from 40° C. to 70° C., to obtain a mixture having a liquid phase and a solid phase;

g) precipitating a solid phase from the liquid of step f) for example by a cooling down step of the mixture to a temperature of 30° C. or less;

h) separating said solid precipitate from the liquid of step g) said liquid comprising a water-rich liquid phase and an oil-rich liquid phase;

i) separating said water-rich liquid phase from said oil-rich liquid phase, j) subjecting said water-rich liquid phase obtained in step i) to one or several membrane filtration(s) to obtain a protein isolate; and k) optionally, drying said protein isolate to obtain a dry protein isolate.

25 Claims, 4 Drawing Sheets

(58) Field of Classification Search
USPC .......................................................... 530/377
See application file for complete search history.

(56) References Cited

U.S. PATENT DOCUMENTS

2010/0010198 A1* 1/2010 Schweizer ................ A23J 3/14
530/377
2010/0249378 A1 9/2010 Wanasundara et al.

OTHER PUBLICATIONS

Garcia-Estepa et al. "Phytic Acid Content in Milled Cereal Products and Breads", Food Research International, (1999), vol. 32, pp. 217-221.

International Search Report and Written Opinion in PCT/EP2018/081263 dated Jan. 22, 2019.

Cheung et al., "Effect of pH and NaCl on the Emulsifying Properties of a Napin Protein Isolate", Food Biophysics, (2015), vol. 10, No. 1, pp. 30-38.

Akbari et al., "An Integrated Method of Isolating Napin and Crucferin from Defatted Canola Meal", LWT—Food Science and Technology, (2015), vol. 64, No. 1, pp. 308-315.

Dendukuri et al., "Oil-Free Protein Isolates from Full Fat, Dehulled Mustard Flour by Microfiltration", Journal of the American Oil Chemists, (2003), vol. 80, No. 3, pp. 287-294.

Nioi et al., "Selective Extraction, Structural Characterization and Antifungal Activity Assessment of Napins from an Industrial Rapeseed Meal", Food Chemistry, (2012), vol. 134, No. 4, pp. 2149-2155.

* cited by examiner

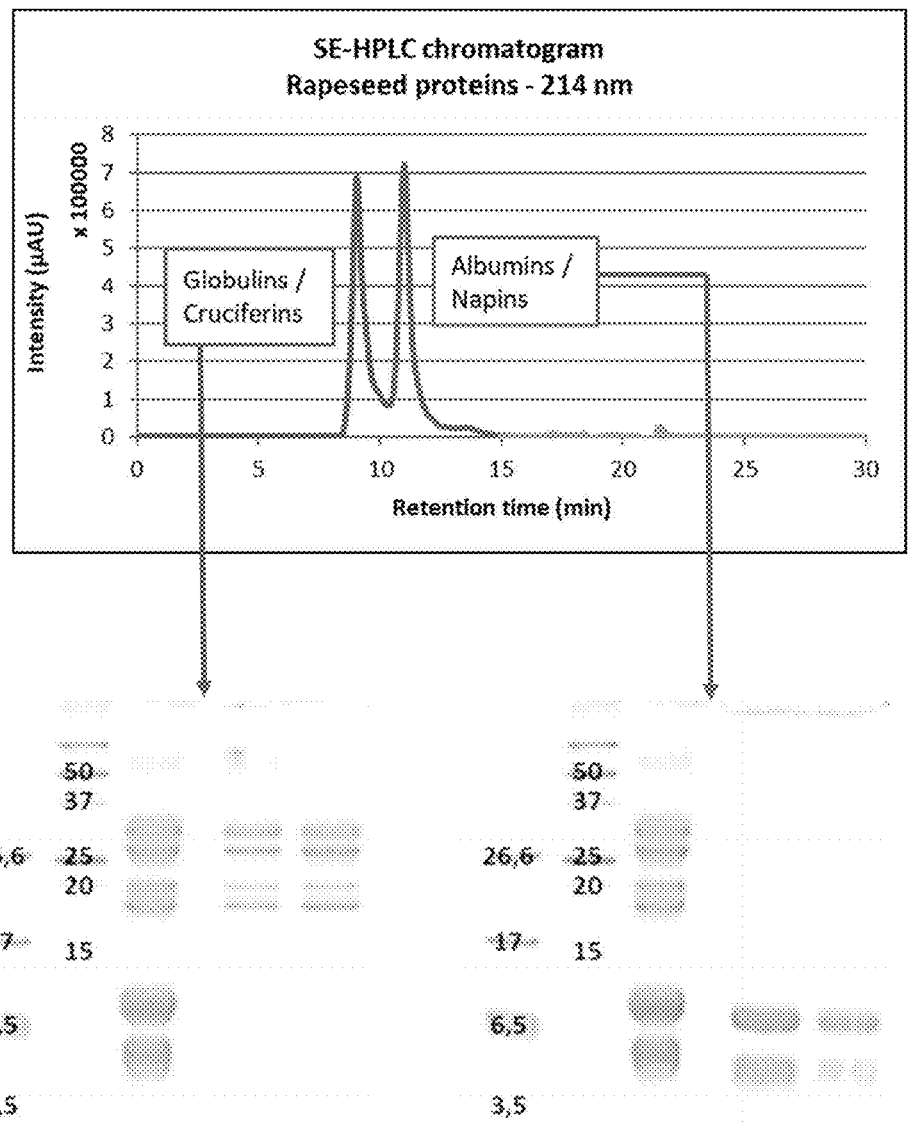
*Figure 4: Chromatogram and associated SDS-PAGE analysis*

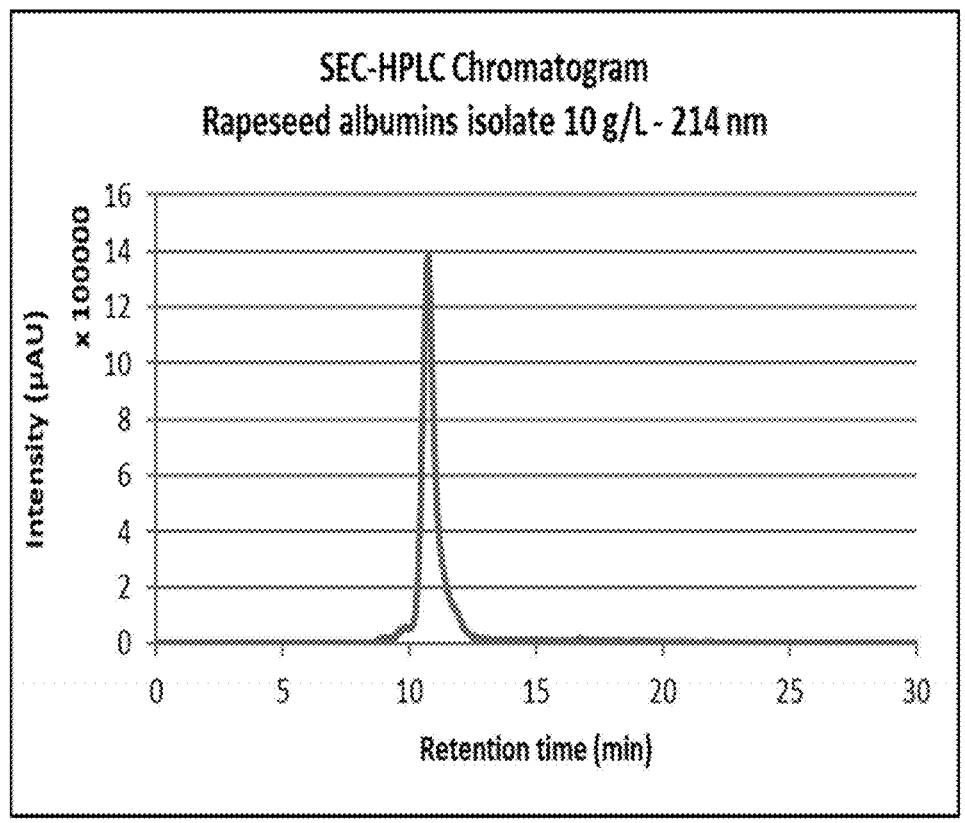
Figure 5: example of a chromatogram of a 10 g/L solution from an albumin isolate

PROTEIN ISOLATE AND PROCESS FOR THE PRODUCTION THEREOF

CROSS-REFERENCE TO RELATED APPLICATIONS

This application is a National Stage Entry of PCT/EP2018/081263, filed Nov. 14, 2018, which claims foreign priority to EP Patent Application No. 17201967.1 filed on Nov. 15, 2017 and EP Patent Application No. 17205565.9 filed on Dec. 5, 2017, the disclosures of which is hereby incorporated by reference in their entirety.

FIELD OF THE INVENTION

The invention relates to a process to extract and/or isolate proteins, and in particular napins, from oilseeds such as rapeseed and sunflower seed. The invention further relates to the products thus obtained.

BACKGROUND OF THE INVENTION

Oil seeds, such as soya bean, rapeseed (also known as canola) and sunflower seed are an important source of proteins having a high nutritional value. In particular, proteins contained in rapeseed are of the albumin type and enable the stabilisation of emulsions and foams. The two major storage proteins in rapeseed are cruciferins (12S globulin) and napins (2S albumin) which respectively represent an average of 50% and 30% in weight of the total protein mass in mature seeds. Cruciferins are oligomeric proteins with at least 6 subunits of two polypeptide chains. Cruciferins have a molecular weight of about 300 kDa although it may range from 230 to 360 kDa. Cruciferins possess emulsifying and gel-forming properties.

Napins are much smaller proteins having a molecular weight ranging from 12 to 15 kDa. They are composed of two polypeptide chains of 4 ($\alpha$) and 9 ($\beta$) kDa ($\beta$), linked by a disulfide bond in its native conformation. Napins have excellent foaming properties which are similar to, or better than, egg albumin. Furthermore, napins have a balanced amino acid composition and include all essential amino acids.

Hence extraction of proteins such as napins, and eventually cruciferins, is of particular interest for use in the food industry. However, rapeseed extracts may have unacceptable amounts of anti-nutrient components such as phytic acid, glycosinolates and sinapic acid. Furthermore phytic acid ((1R,2R,3S,4S,5R,6S)-cyclohexane-1,2,3,4,5,6-hexayl hexakis[dihydrogen (phosphate)]) is a component that, when present, has adverse effects on the ability of proteins to solubilize in water at fairly low concentration. A weight concentration of above 10, or even 5, wt % of phytic acid in respect of the total weight of the protein will substantially prevent the napins to solubilize in water and will render them unsuitable as, inter alia, a food ingredient.

Phytic acid is also an anti-nutritional compound insofar as it decreases the bioavailability of minerals and because it forms with proteins a complex which is slightly degraded by digestive enzymes. For all these reasons removal of all or most of the naturally occurring phytic acid is an essential step in order to achieve a napin-based extract, isolate or composition of high nutritional and economical value.

In order to purify the proteins from a liquid extract, it is possible to precipitate them by adding a high concentration of ammonium sulfate as a kosmotropic agent. Doing so, the amount of water available for protein solvation dramatically decreases resulting in selective protein precipitations. As a consequence, proteins can be then separated from, amongst other anti-nutritional compounds, phytic acid. However, when napin is concerned, the concentration of ammonium sulfate required to precipitate the protein approach 6 M. Such a method is therefore not appropriate to a large scale extraction process due to the costs and pollution involved by using such high concentration of precipitating agent.

Nioi et al. "Selective extraction, structural characterization and antifungal activity" Food Chem. 134 (2012) 2149-2155] describes a process to obtain Napin at laboratory scale. The best extraction conditions were observed at pH 2, 12% (w/w) of rapeseed meal in water after 15 min of extraction at room temperature. Under these conditions the extraction was selective. The napin proteins were precipitated from extracted liquid phase obtained after centrifugation at 65% of ammonium sulfate saturation and re-suspended in water at a third of the initial volume. The purity of the obtained napin isolate was 92%. However, the high concentrations of ammonium sulfate needed to obtain precipitation of the napin proteins are not suitable on an industrial scale. Furthermore, when an industrial known technique of purification, i.e. micro and ultrafiltration, was applied to Nioi to replace the use of a precipitant, the resulting powder contained an amount of 8.4 wt % of phytic acid in respect of the total weight of proteins contained in the powder. As aforementioned such an amount is too high for a viable commercial product.

It is therefore highly desirable to provide a high yield process to obtain a composition comprising, consisting of, or essentially consisting of low molecular weight napin-type proteins with a low or negligible amount of phytic acid and/or high solubilisation properties in water as well as such a composition.

Alternatively, or additionally it is also highly desirable to provide a composition consisting essentially of low molecular weight napin-type proteins with negligible amount of phytic acid and/or high solubilisation properties in water.

Akbar, J. Wu/LWT—Food Science and Technology 64 (2015) 308-315 describes a napin and cruciferin extraction from an hexane defatted canola meal using acidic washing (pH 4), alkaline extraction (pH 12.5), isoelectric precipitation (pH 4), and ultrafiltration. Although a low level of phytic acid in the napin extract was achieved, the napin content was relatively low (81.9%±1.2 w/w).

Cheung et al. in "Effect of pH and NaCl on the Emulsifying Properties of a Napin Protein Isolate" (Food Biophysics (2015) 10:30-38) describes a napin and cruciferin extraction process from an hexane defatted canola meal comprising the steps of performing aqueous extraction of the Brassicaceae oilseed meal at a pH of from about 2.5 to about 5.0 to obtain a soluble napin-rich protein extract and a cruciferin-residue. This step is carried out using a low amount of salt (0.75% w/v) and the napin concentration is unknown.

SUMMARY OF THE INVENTION

It is one object of the invention to overcome this drawback and provide a process for the extraction/purification of proteins, in particular low molecular weight proteins from an oilseed meal which results in a protein extract which has little or no phytic acid. Advantageously the process may also achieve high yielding and/or high purity of protein extracts.

BRIEF DESCRIPTION OF THE DRAWINGS

FIG. 4 is a chromatogram and associated SDS-PAGE analysis of a typical rapeseed isolate of the disclosure.

FIG. 5 is a chromatogram of a napin isolate in a 10 g/L solution.

DETAILED DESCRIPTION

Figure 1:
FIG. 1 is a picture of the composition obtained according to Example 2 of the disclosure.

According to an aspect of the invention, it is provided a process for the production of a protein isolate from an oilseed meal, said isolate comprising proteins and an amount of 4 wt % or less, preferably 3 wt % or less, and most preferably 2 wt % or less, of phytic acid, said amount of phytic acid being by total weight of said proteins. This process comprises the following steps:
  a. providing an oilseed meal;
  b. mixing the oilseed meal with a first aqueous solvent to form a slurry at a pH ranging from 6 to 7.8, said slurry having a solid phase;
  c. separating said solid phase from said slurry,
  d. mixing said separated solid phase with a second aqueous solvent at a pH ranging from 1 to 3.5, preferably from 2 to 3, to form a mixture said mixture having a liquid phase;
  e. separating said liquid phase from said mixture formed in step d);
  f. f1) mixing the separated liquid phase to a phytase at a temperature and a pH suitable for phytase activity to obtain a mixture having a liquid phase and a solid phase;
  and/or
  f2) mixing the separated liquid to a salt, to obtain a resulting liquid composition having a molar concentration of said salt ranging from 0.01 M to 0.5 M, at a temperature ranging from 40° C. to 70° C., to obtain a mixture having a liquid phase and a solid phase;
  g. precipitating a solid phase from the liquid of step f) for example by a cooling down step of the mixture to a temperature of 30° C. or less;
  h. separating said solid precipitate from the liquid of step g) said liquid comprising a water-rich liquid phase and an oil-rich liquid phase;
  i. separating said water-rich liquid phase from said oil-rich liquid phase,
  j. subjecting said water-rich liquid phase obtained in step i) to one or several membrane filtration(s) to obtain a protein isolate; and
  k. optionally, drying said protein isolate to obtain a dry protein isolate.

Step a)

The oilseed meal to be used may be any of the ones described hereinbelow and/or prepared.

Step b)

The first aqueous solvent of step b) is a liquid able to extract water soluble proteins and which is essentially constituted of water, that is which at least comprises 80 wt % of water by total weight of the aqueous solvent. Advantageously the aqueous solvent consists, or consists essentially of water. The aqueous solvent may consist of any type of available water, such as tap water. It may further include a small proportion (e.g. less than 20 wt %, 15 wt %, 10 wt %, 5 wt %, 2 wt % or 1 wt %) of at least another component. Such other component can be a compound naturally occurring in the water or added on purpose to adjust the pH of the slurry of step b). For example, it can be a mineral or a salt such as an alkali, e.g. NaOH. If a salt is present, then it is advantageously NaCl, KCl or $CaCl_2$), preferably NaCl. The pH adjustment, if required can be carried out by the addition of an aqueous solution of NaOH at 1 M. It is preferred not to use solvent such as methanol, propanol, iso-propanol, tetrahydrofuran, etc. In particular, it is preferred that no organic solvent is used in the aqueous solvent used in step b). However, if an organic solvent (i.e. a compound with a carbon chain) is to be used, it should only be present in amount less than 20 wt %, 15 wt %, 10 wt %, 5 wt %, 2 wt %, or 1 wt % so that their presence in the final product can be reduced to an acceptable or negligible amount.

The oilseed meal and the first aqueous solvent are mixed together using conventional method to form a slurry which contain dissolved proteins, and may further contained a suspension of protein, oil and optionally fibers as well as anti-nutritional compounds. The weight ratio of (preferably partially defatted) oilseed meal/first aqueous solvent (preferably water) usually ranges from 1:5 to 1:20 (w/w), preferably 1:6 to 1:10 (w/w) and more preferably about 1:8 (w/w).

The temperature of the slurry is preferably above room temperature. It particular it may range from 40 to 70° C., preferably from 50 to 60° C. (e.g. around 55° C.).

The pH of the slurry is adjusted at a pH ranging from 6 to 7.8, preferably from 6.8 to 7.5, using, for example a concentrated solution of NaOH.

Once the pH is adjusted, step b) is usually carried out, usually under stirring or agitation for a time period ranging from 10 minutes to 2 hours, preferably 30 to 70 minutes (e.g. around 45 minutes or around 1 hour).

Step b) can be carried out with or without a preliminary step of phytase digestion by the addition of a phytase. If a phytase is first used, the mixture is first left for a given period of time to a digestion step to take place. This can last from 40 minutes to 90 minutes, preferably an hour. After such a period of time, the pH is then preferably adjusted around 6.8±0.1. Also, when a phytase is used, a liquid/solid extraction step, such as the one described in step c) hereinafter, is carried out and the solid fraction (wet cake) obtained washed with water, preferably at room temperature (or at a temperature ranging from 52 to 60° C. in view of microbial concerns) before step c) is performed. If a phytase is not used, the pH applied is preferably adjusted around 7.2±0.3.

It is believed that such a phytase preliminary step is not required to obtain the desired Low Molecular Weight Proteins (LMWP) extract. However, it may be advantageous in a process where both LMWP and High Molecular Weight Proteins (HMWP) are to be extracted and/or isolated from an oilseed meal.

Step c)

Once step b) is carried out (with or without a phytase digestion step and with or without an aqueous washing step of the solids) a solid phase is separated from the slurry. The means to carry out this separation are well known in the art and include centrifugation means, such as a decanter centrifuge, filtration means, pressing means, such a screw press, a filter press, a belt press, a French press, decantation means, and/or any other means that separates the slurry into a solid phase and a liquid phase. This separation may be performed using decanter centrifuge, for example at g force ranging from 2,000 to 6,000 g, preferably from 3,000 to 5,000 g, for example about 4,600 g. As the skilled person will directly understand the solid phase contains a small proportion of liquid and conversely the liquid phase will comprise a small proportion of solids or solid particles. Hence in a particular embodiment of the invention the liquid phase containing residual solids is further subjected to another separation step using for example at least one disk stack centrifuge. The g-force of this centrifugation may be ranging from 6,000 to 20,000 g, optionally 17,000 g. According to a preferred embodiment the solid-rich sludge obtained from this centrifugation of the liquid phase is added to solid phase obtained in step c) in order to carry out the extraction step d).

Step d)

The solid phase is enriched in water-insoluble proteins and may or may not comprise a solid-enriched sludge obtained from the further processing of the liquid phase obtained in step c) solids.

The second aqueous solvent of step d) is a liquid able to extract water soluble proteins and which is essentially constituted of water, that is which at least comprises 80 wt % of water by total weight of the aqueous solvent. Advantageously the aqueous solvent consists, or consists essentially of water. The aqueous solvent may consist of any type of available water, such as tap water. It may further include a small proportion (e.g. less than 20 wt %, 15 wt %, 10 wt %, 5 wt %, 2 wt % or 1 wt %) of at least another component. Such other component can be a compound naturally occurring in the water or added on purpose to adjust the pH of the mixture of step d). For example, it can be a mineral or a salt such as an acid acceptable for use in food or feed, e.g. hydrochloric acid, phosphoric acid, sulfuric acid, lactic acid, citric acid, preferably phosphoric acid. If a salt is present, then it is advantageously NaCl, KCl or $CaCl_2$), preferably NaCl. If Step d) includes a pH adjustment, it can be carried out by the addition of an aqueous solution of said acid, or a mixture thereof.

It is preferred not to use solvent such as methanol, propanol, iso-propanol, tetrahydrofuran, etc. In particular, it is preferred that no organic solvent be used in the second aqueous solvent used in step d). However, if an organic solvent (i.e. a compound with a carbon chain) is to be used, it should only be present in amount less than 20 wt %, 15 wt %, 10 wt %, 5 wt %, 2 wt %, or 1 wt % so that their presence in the final product can be reduced to an acceptable or negligible amount.

The solid phase and the second aqueous solvent are mixed together to form a mixture which contain dissolved proteins, and may further contain a suspension of protein, oil and optionally fibers as well as anti-nutritional compounds. The pH of the mixture is adjusted at a pH ranging from 1 to 3.5, preferably from 2 to 3.

The solids-rich phase and the second aqueous solvent are mixed together using conventional method to form a mixture or slurry which contain dissolved proteins, and may further contained a suspension of proteins, oil and optionally fibers as well as anti-nutritional compounds. The ratio of solid phase/second aqueous solvent (preferably water) usually ranges from 1:2 to 1:12 e.g. about 1:3 (w/w) or preferably with a dry matter content ranging from 4% and 15%.

The temperature of the mixture is preferably room temperature. In particular, it may range from 15 to 60° C., preferably from 15 to 25° C. (e.g. around 18° C.).

The pH of the slurry is adjusted at a pH ranging from 1 to 4, preferably from 1.5 to 3, for example a pH of around 2, using, for example a concentrated solution of phosphoric acid (at, for example, a concentration of 1 M or 2 M in water) or HCl (at, for example, a concentration of 1 M in water).

Once the pH is adjusted, step d) is usually carried out, preferably under stirring or agitation, for a time period ranging from 5 minutes to 2 hours, preferably 10 minutes to 60 minutes (e.g. from 20 to 30 minutes).

Step e)

The liquid phase of the slurry is then separated. The means to carry out this separation are well known in the art and include centrifugation means, such as a decanter centrifuge, filtration means, pressing means, such a screw press, a filter press, a belt press, a French press, decantation means, and/or any other means that separates the slurry into a solid phase and a liquid phase. This separation may be performed using decanter centrifuge, for example at g force ranging from 2000 to 20000 g, preferably from 3000 to 17000 g, in particular at about 4600 g, or 15000 g. This force can be applied from a few minutes to up to 1, or 2, hours. As the skilled person will directly understand the liquid phase may comprise a small proportion of solids or solid particulates. Hence in a particular embodiment of the invention the liquid phase containing residual solids may be further subjected to another separation step using for example at least one disk stack centrifuge.

According to another embodiment of the invention a filtration solid/liquid of the supernatant obtained from the first separation of step e) can be performed (e.g. using a Whatman filter). The filtrate can further be subjected to a further centrifugation step (such as the one above described (e.g. 15000 g). The liquid supernatant is recovered and processed in step f).

The liquid phase thus obtained is enriched in water soluble proteins.

Step f)

This liquid phase is then subjected to a phytic acid removing step f) which can be the step described as f1) and/or f2).

Step f1)

According to a particularly preferred variant of the invention, the separated liquid may then be contacted, in a step f1) to a phytase enzyme of the type E.C 3.1.3.x (Phosphoric monoester hydrolase phosphatase) at a temperature and a pH suitable for phytase activity. Such enzyme is commercially available and may come from a microorganism or yeast such as *Aspergillus niger*. For example, the phytase sold under the name Phytase Maxamyl™ (cf. infra) is suitable to carry out the invention. In order to enhance phytase activity the temperature can be advantageously adjusted in a range from 40° C. to 70° C., preferably from 50° C. to 60° C., more preferably from 53° C. to 57° C., and most preferably at 55° C. Suitable pH may be chosen in the range from 3.8 to 5.5, preferably from 4 to 5. A pH of 4.3±0.2 was unexpectedly found to provide good results even though the recommended pH is usually higher (around pH 5). The pH may be adjusted by the addition of a solution of an alkali such as NaOH 1 M in water. The step f1) enables the digestion of phytic acid and may last for any suitable time period, such as from 15 to 240 min, preferably 60 min. As usual, continuous stirring is applied. Step f1) usually takes from 40 to 90 minutes, preferably an hour. The quantity of phytase used is preferably of about 1 wt % in respect of the weight of the dry matter of liquid phase obtained in step e). In an advantageous embodiment the temperature is ranging from 40° C. to 70° C., preferably from 50° C. to 60° C., more preferably from 53° C. to 57° C., and most preferably at 55° C., and the pH is range is in a range from 3.8 to 5.5 (with an alkali, e.g., NaOH 1 M), preferably from 4 to 5.

Step f2)

Alternatively, according another variant of the invention, the separated liquid can be mixed, in a step f2), to a salt, such as NaCl, KCl or $CaCl_2$), preferably NaCl, to obtain a resulting liquid composition having a molar concentration of said salt ranging, for example, from a saturated solution, or a solution in water of 0.01 M to 0.5 M, preferably 0.05 M to 0.5 M, or 0.05 M to 2 M, preferably from 0.1 M to 1 M (in particular around 0.5 M). A concentration of around 0.5 M±10% has shown particular efficacy. A range of 0.2 M to 0.5 M, or more particularly of 0.3 M to 0.5 M, is of particular benefit for putting the process of the invention into practice. The temperature is advantageously set at a temperature ranging from 40° C. to 70° C., preferably from 50° C. to 60° C., more preferably at 55° C. This temperature of around 55° C. (i.e. ±2° C.) has shown particular efficacy. The mixture may be stirred for any suitable time, for example from 15 to 240 min, preferably 60 min. Eventually the pH of the medium can advantageously be adjusted to range from 1 to 3.5, preferably from 2 to 3. In order to set the pH, one of the acids used in step d) can be used.

According to another variant of the invention the alternative steps f1) and f2) could be used in combination.

The step f) which comprises step f1) and/or f2) allows the degradation of phytic acid and/or the separation of said acid from napin proteins.

Step g)

This step allows for the precipitation of some of the mixture obtained in step f). As this step is preferably carried out at a temperature higher than the ambient temperature, a suitable precipitating agent is a decrease of temperature. In such a step the temperature is lowered down (e.g. let to cool down) to approximately 30° C. or less, preferably to a temperature ranging from 10° C. to 25° C. The precipitate forms a solid phase.

Step h)

The liquid is separated from the solid precipitate using one of the centrifugation means previously described in step c) or step e). It is preferred that such separation is carried out using first a decanter centrifuge applying a g-force which may ranging from 15000 g to 20000 g, in particular around 17000 g.

The solid phase being removed from the medium and the liquid phase is then treated to obtain an oil-rich phase and a water-rich phase. These two liquid phases having low mutual solubility can separate spontaneously. The treatment allowing phase separation, step i), may therefore be a simple decantation. However other treatments to separate liquid phases well known by the skilled person and described above in respect of step c) and e) can be used. In this step the separation includes, for example, centrifugation.

Step i)

The liquid phase recovered, if it contains two immiscible liquid phases, may then be treated in order to separate a "light", or higher, liquid phase, which is oil-rich, from a "heavy", or lower, phase which is water or protein-rich. The terminology "oil-rich" or "protein-rich" is, of course, relative and simply means that one of the phases has a higher proportion in weight content of oil or protein with respect to the other phase. This step, or skimming step, can be carried out using a skimmer such as for example, a skimming centrifuge, a 2-phase centrifuge or a 3-phase centrifuge. A 3 phases disk stack skimmer is preferred.

Step j)

The "heavy" or aqueous liquid phase extracted from step i) is protein-rich and is subjected to, microfiltration (and diafiltration), ultrafiltration and/or ultrafiltration followed by diafiltration to recover a purified protein solution. As it is common practice, several, i.e. more than two diavolumes can advantageously be used. The filtration removes most or at least one member of the group of compounds constituted of solubilised phytic acid, phytic acid derivatives, sugars, phenolic compounds, free nitrogen, mineral compounds and mixture thereof.

A first filtration step using microfiltration is preferred. Such a microfiltration may be performed by using filtration membrane having a nominal pore size ranging from 0.1 μm to 2 μm, preferably from 0.1 μm to 1 μm. Microfiltration may, as it is usual, comprise one or more diavolume with water. Furthermore, the pH may advantageously be controlled and/or adjusted, for some or all the filtration and/or the diafiltration steps. In order to adjust the pH a pH modifier can be added, e.g. phosphoric acid, to the water. Such a controlled pH can advantageously be chosen at around 4.5, e.g. 4.3.

Subsequently or alternatively ultrafiltration/diafiltration can be used. The ultrafiltration is preferably carried out using a filtering device made of a suitable material such as a polysulfone (PS) or a polyethersulfone (PES) which has high protein retention. The molecular weight cut-off (MWCO) of the filter material may range from 3 kDa to 10 kDa, preferably 3 to 5 kDa. Furthermore, the pH may advantageously be controlled and/or adjusted, e.g. around 4.5, e.g. 4.3, for some (e.g. the first or the few firsts) or all the filtration and/or the diafiltration steps. In order to adjust the pH, a pH modifier can be added, e.g. phosphoric acid to the water. In a preferred embodiment the temperature can also be elevated either slightly (e.g. around 30° C.) or more positively (e.g. around 55° C.).

Step k)

In order to preserve the albumin type proteins thus isolated by the process of the invention, it is advantageous to freeze dry, or lyophilized or to spray dry the purified protein solution to obtain a dry powder. Beforehand, the purified proteins are frozen between −80° C. and −20° C. until complete freezing. Then freeze-drying is carried out by the use of a standard freeze dried apparatus at a sublimation temperature around −20° C., or standard vertical spray dryer equipped with nozzle, with an inlet temperature ranging from 150° C. to 200° C. and an outlet temperature ranging from 70 to 90° C. in order to achieve a powder with less than 7 wt % water, and preferentially 4 to 6 wt %.

The process of the invention further encompasses a process where any one of steps c), e), h), i) and/or j) may be repeated. According to another embodiment of the invention any or all of steps a) to e), i) and j) may be conducted at room temperature, that is at a temperature ranging from 15° C. and 30° C.

According to a variant of the invention, the process of the invention does not necessarily comprise steps b) and c) above described. A low phytic acid content may be obtained without these steps. In this embodiment, an oilseed meal can be directly subjected to step d) above described. According to this variant all preferred embodiments and features above described in respect of above steps a), and d) to k) can be used in or applied to this particular process. Moreover, according to a particularly preferred embodiment of this variant, step f1) is the step used in this method. Hence, according to this particularly preferred embodiment it may be provided a process for producing a protein isolate from an oilseed meal, said isolate comprising proteins and an amount of 4% or less, preferably 3 wt. % or less of, more preferably less than 2%, of phytic acid, said amount of phytic acid being by weight of proteins in said isolate, said process comprising the following steps:

i. providing an oilseed meal;
ii. mixing said oilseed meal with an aqueous solvent at a pH ranging from 1 to 3.5, preferably from 2 to 3, to form a mixture said mixture having a liquid phase;
iii. separating said liquid phase from said mixture formed in step ii);
iv. mixing the separated liquid phase to a phytase at a temperature and a pH suitable for phytase activity to obtain a mixture having a liquid phase and a solid phase;
and/or
v. precipitating a solid phase from the liquid of step iv) by a cooling down step of the mixture to a temperature of 30° C. or less;
vi. separating said solid precipitate from the liquid of step v) said liquid comprising a water-rich liquid phase and an oil-rich liquid phase;
vii. separating said water-rich liquid phase from said oil-rich liquid phase,
viii. subjecting said water-rich liquid phase obtained in step vii) to one or several membrane filtration(s) to obtain a protein isolate; and
ix. optionally, drying said protein isolate to obtain a dry protein isolate.

According to another variant of the invention, the process of the invention comprises the following steps:
A. providing an oilseed meal
B. mixing the oilseed meal with a first aqueous solvent to form a slurry at a pH ranging from 6 to 7.8, said slurry having a liquid phase;
C. separating said liquid phase from said slurry,
D. adjusting the pH of said separated liquid phase at a pH ranging from 2 to 4, preferably from 3 to 3.8, to form a mixture said mixture having a liquid phase and a solid precipitate;
E. separating said liquid phase from said solid precipitate;
F. subjecting the liquid phase obtained in step E. to a microfiltration step and recovering a permeate;
G. subjecting said permeate of step F. to an ultrafiltration step which is followed by at least one diafiltration step carried out with an aqueous solution of a salt such as NaCl or $CaCl_2$), preferably NaCl, 0.05 M-0.5 M, preferably 0.1 M-0.3 M to obtain a protein isolate of low molecular weight, and
H. optionally, drying said protein isolate to obtain a dry protein isolate.

This process produces a protein isolate from an oilseed meal, said isolate comprising proteins and an amount of 4 wt. % or less, preferably 3% or less, more preferably of 2% or less, of phytic acid, said amount of phytic acid being by weight of proteins in said isolate, said process comprising the following steps:

Step A.
The oilseed meal to be used may be any of the ones described herein below.

Step B.
Step B. is as described in step b) hereinabove and all preferred embodiments and features above described in respect of step b) can be used in or applied to this particular process.

Step C.
In this step C. the slurry is separated in a liquid phase and a (more) solid one. Once step B.) is carried out (with or without a phytase digestion step and with or without an aqueous washing step of the solids) the slurry is separated into a liquid phase and a solid one. The means to carry out this separation are well known in the art and include centrifugation means, such as a decanter centrifuge, filtration means, pressing means, such a screw press, a filter press, a belt press, a French press, decantation means, and/or any other means that separates the slurry into a solid phase and a liquid phase. This separation may be performed using decanter centrifuge, for example at g force ranging from 2000 to 6000 g, preferably from 3000 to 5000 g, for example about 4600 g. As the skilled person will directly understand the solid phase contains a small proportion of liquid and conversely the liquid phase will comprise a small proportion of solids or solid particulates. Hence in a particular embodiment of the invention the liquid phase containing residual solids is further subjected to another separation step using for example at least one disk stack centrifuge. The g-force of this centrifugation may be ranging from 10000 to 20000 g, optionally 17000 g. Furthermore, it is also preferred that the liquid phase was reheated, e.g. 55° C.

Step D.
In step D. the pH is adjusted in order to obtain the precipitation of solids. pH adjustment can be carried out by the addition of an aqueous solution of an acid, or a mixture thereof. Such an acid acceptable for use in food or feed can be hydrochloric acid, phosphoric acid, sulfuric acid, lactic acid, citric acid, preferably phosphoric acid. For example, a solution of phosphoric acid at a concentration of e.g. 1 M.

Step E.
In step E. the solid precipitate is removed to obtain a liquid phase. The means to carry out this removal are similar to one described in respect of step h) which is above described. According to this variant all preferred embodiments and features above described in respect of above step h) can be used in or applied to this particular process step.

According to an embodiment of the process the solid precipitate can be washed (e.g. by dilution in hot water such as 55° C.) to obtain a washed precipitated and diluted liquid phase. Said diluted liquid phase is advantageously added to the liquid phase obtained in Step E. The washing step is preferably carried out at and acidic pH (from about 3 to about 4, e.g. 3.5). Furthermore, an additional clarification step can be carried out after the washing step to better separate the precipitate (or sludge) from the diluted liquid phase.

Step F.
The liquid phase, which may comprise an additional diluted liquid phase obtained extracted from the precipitates, is then subjected to microfiltration step. Such a microfiltration may be performed by using filtration membrane having a nominal pore size ranging from 0.1 μm to 2 μm, preferably from 0.1 μm to 1 μm (e.g. 0.1 μm). Microfiltration may, as it is usual, comprise one or more diafiltration step with water. Furthermore, the pH may advantageously be controlled and/or adjusted, for some or all the filtration and/or the diafiltration steps. In order to adjust the pH a pH modifier can be added, e.g. phosphoric acid, to the water. Such a controlled pH can advantageously be chosen around 3.5. The liquid can be concentrated several times, e.g. more than 5.

Step G.
Subsequently or alternatively ultrafiltration can be used. The ultrafiltration is preferably carried out using a filtering device made of a suitable material such as a polysulfone (PS) or a polyethersulfone (PES) which has low protein retention. The molecular weight cut-off (MWCO) of the filter material may ranges from 3 kDa to 10 kDa, preferably 3 to 5 kDa. Ultrafiltration may, as it is usual, comprise one or more subsequent diafiltration step. At least one and preferably more than one (e.g. 2 or 3) diafiltration step is carried out using an aqueous solution of salt, for example NaCl or CaCl$_2$), preferably NaCl at a suitable concentration. Such concentration may be ranging from 0.05 M to 0.5 M, preferably from 0.1 M to 0.3 M. According to preferred embodiment the dia-ultrafiltration step with salted water can be carried out after an ultrafiltration step (which may include several dia-ultrafiltration steps) which is carried out with water (and not salted water), possibly at an elevated temperature (e.g. 55° C.). Additionally, or alternatively, a pasteurizing step can further be carried out before that the dia-ultrafiltration with salted water takes place. Such a pasteurizing step can take place at 75° C. for 15 minutes. In a preferred embodiment the temperature can also be elevated either slightly (e.g. around 30° C.) or more positively (e.g. around 55° C.).

Step H.

Step H. is as described in step k) hereinabove and all preferred embodiments and features above described in respect of step b) can be used in or applied to this particular process step.

According to a further embodiment of the invention it is preferred that none of the methods of the invention comprise a step where the proteins to be isolated are precipitated using ammonium sulphate or a highly concentrated protein precipitant or coagulant. Concentration of higher than 5 M are usually not environmentally friendly.

A further object of the invention is a protein isolate obtainable or obtained by the processes above described and having at most 4 wt. % of phytic acid, preferably less than 3 wt. % and more preferably less than 2 wt. %, by weight of total proteins in said isolate. Preferably the isolate has also a purity of at least 85 wt. %, preferably at least 90% (N×6.25) on a dry protein isolate.

Preferably the isolate is composed of at least 90 wt. %, preferably at least 95% of albumin (napin) on the total proteins.

It is further preferred that the proteins are napin (2S albumin) and/or that the isolate be a napin isolate.

According to a very much preferred embodiment the proteins contained in the isolate are native protein (i.e. in a native conformation) and not hydrolysed.

The protein isolate thus obtained according to the method of the invention has a solubility in water at least superior, or equal, to 90% at pH 5, preferably superior or equal to 95% at pH5, even superior or equal to 98% at pH 5.

Alternatively, or additionally, the protein isolate thus obtained according to the method of the invention has a water-solubility at least superior, or equal, to 90% at pH 7, preferably superior or equal to 95% at pH7, even superior or equal to 98% at pH 7.

The use of such an isolate according to the invention in the food industry, for example as emulsifier or as foaming agent or to enrich lysine and/or cysteine and/or methionine contents on protein, is also part of the invention.

Such an isolate could be used in food product or food ingredient, preferably for beverages, such as acidic beverage with a pH value less than 5, drinks with at least 1% protein content, coffee preparation including a whitener or not, is also part of the invention.

Oilseed Meal

The term «oilseed meal» as used herein refers to a meal prepared from an oilseed in which the oilseed has been ground and crushed to form a meal. Oil may have been extracted either partially or totally from the oilseed meal to form what is known in the art as a «pressed cake» or a (partially) «defatted meal». To obtain a defatted meal, solvent can be used for example, hydrophobic solvents such as pentane, hexane and/or other refrigerants such as iodotrifluoromethane (ITFM) and R134a (1,1,1,2-tetrafluoroethane), to remove or reduce residual oil from the seedcake. When such organic solvents are used the oil content remaining in the pressed cake is residual (e.g. ranging from 0.1 to 4 wt % by total weight of the pressed cake.

Although, as shown in the examples, any of these meals may be used, it is preferred to use a cold pressed meal which is partially defatted. By "cold pressed" it is particularly meant that the oilseed meal has been cold-pressed at a temperature of 85° C. or less, more preferably 60° C. or less. The defatted meal usually contains dry matters in a proportion ranging from 80 wt % to 98 wt % in respect of the defatted meal total weight. The dry matter content will depend upon the method used for oil extraction. Usually a cold pressed defatted meal will have a dry matter content of 89 to 92 wt % (e.g. 91% wt). When an organic solvent is used the dry matter content usually increases and may range from 92 wt % to 96 wt %. The pressed meal may comprise about 15 wt % to about 50 wt % of proteins and from about 5 wt % to about 20 wt % of oil, by total weight of the dry matter of defatted meal. Typically, such a meal may contain from about 18 wt % to about 26 wt. % of proteins and from about 13 wt % to about 22 wt % of oil, by total weight of the defatted meal. It is particularly preferred that no hexane be used to extract oil from the oilseed meal. It is further preferred that no organic solvent be used to extract oil from the oilseed meal. The process of the invention is particularly suitable to the extraction of cold pressed oilseed meals which are generally considered more difficult to process.

The amount of phytic acid that is present in the oilseed meal to be used in a process according to the invention is usually superior to 4 wt. % of the proteins' total weight contained within meal. Usually the amount of phytic acid is much higher, usually it may range from 8 to 30 wt. %, for example from 10 to 20 wt. %.

According to an embodiment of the invention the oilseed meal is a partially defatted meal, a defatted meal or a protein enriched meal.

The invention also encompasses the use of an oilseed meal which has been processed in order to extract other substances than its oil. However, this embodiment is not particularly preferred. For example, an oilseed meal from which some proteins have already been extracted can be used according to a process of the invention. According to a preferred embodiment the oilseed meal from the invention can be a (partially) defatted oilseed meal from which high molecular weight proteins (HMWP), such as cruciferins, have been extracted. Such a meal will be referred to as an oilseed meal having high "low molecular weight proteins" (LMWP) proteins contents. A high molecular weight protein within the meaning of the invention can be defined as an oil seed protein having a molecular weight superior to 200 kDa, preferably ranging from 220 to 400 kDa. A low molecular weight protein within the meaning of the invention can be defined as an oil seed protein having a molecular weight inferior to 20 kDa, preferably ranging from 4 to 15 kDa, evaluated by SDS-PAGE analysis. Such a LMWP is preferably a reserve protein, especially an albumin-type protein. The most preferred amongst the LMWP is napin-type proteins.

According to a preferred embodiment of the invention, the oilseeds are first dehulled, at least partially (e.g. 80%) before being transformed into an oilseed meal. The use of dehulled seed has shown to be particularly effective to extract a high level of proteins.

While the process is exemplified in particular in respect of the processing of rapeseed and rapeseed meals, other oil seeds and their meals, including, but not limited to, mustard seed, broccoli seed, flax seed, cotton seed, hemp seed, sunflower seed, sesame seed and soybean meal, can be processed in the same manner to provide high protein content end products. Rapeseed (canola) as well as sunflower seed are particularly preferred.

The term «rapeseed» encompasses all subspecies of *Brassica napus* subsp. *napus* including Argentine canola, canola, colza, oilseed rape, and rape.

Isolate

Proteins are available as hydrolysates, concentrates and isolates. Hydrolysates are proteins that have been partially broken down and unfolded by exposing them to heat, acid or enzymes to break apart some bonds linking amino acids and make them more digestible. Many protein extracts are concentrates which have a content of around 80% by total weight of proteins.

The isolate of the invention is preferably a native protein isolate having a protein content of at least 85 wt. %, usually at least 90 wt % and more advantageously more than 93 wt % by total weight of the proteins. Proteins content is measured on dry matter by determining the nitrogen content using the Kjeldahl method (see infra) and multiplying it by a standard conversion factor of 6.25 (i.e. N×6.25 conversion factor). Although this is a widely accepted measurement in the art its does include some uncertainty. Hence protein contents of above and over 100% can be measured. However as this is the standard measure in the art, this is the measure which will be adopted to define the expression "protein content" within the meaning of the invention. Napin proteins will be identified by a molecular weight of 14 kDa measured by SDS-PAGE. According to a particular embodiment of the invention, the isolate which can be obtained by the process of the invention will have at least 90% wt of napin proteins.

The method of the invention is particularly suited to the extraction of LMWP storage proteins such as napins, which are extracted from rapeseed. However, the method of the invention could be directly applied to other oilseed such as sunflower in order to extract similar LMWP storage protein of the albumin type.

According to a preferred embodiment the protein isolate of the invention has a light beige colour.

EXAMPLES

The following analysis results (determination of protein content, of phytic acid, solubility, SE-HPLC) and described in the examples were repeated at least twice. Thus the results provided are their average.

Examples 1 to 3: Napin Production from a Globulin-Poor Rapeseed Meal

These two examples are carried out on a partially defatted dehulled rapeseed meal which was obtained as follows:

1) Dehulled Rapeseed Cold Press Meal Production

For dehulled rapeseed cold press meal production, whole seeds were firstly dehulled with a ripple flow machine to open the seed. The mixture containing free hulls was separated with fluid bed separator to remove the hulls. The residual whole seeds in the kernel-rich phase were separated with Denis D50 separator and whole seeds were recycled to the ripple flow machine for dehulling. After Denis D50 separation, the dehulling level was characterized by image analysis. A target of 80% of dehulling was fixed for rapeseed cold press meal production. The kernel-rich meal was pressed with a MBU20 press (OLEXA) to get dehulled rapeseed cold press meal with residual oil content of around 15% without exceeding 60° C. on meal at the end of the pressing step.

2) Starting Material Production for Example 1 to 3

For the production of the oilseed meal 150 kg of rapeseed cold press meal (Table 1) was mixed with 55° C. tap water, in a 1:8 meal:water ratio (w/w) to form a slurry. The slurry was agitated at 160 rpm during 10 minutes and phytase Maxamyl P (DSM) was added (in ratio of 1% of meal) without pH adjustment. After one hour of phytase digestion, the pH of the slurry was adjusted to 6.8 with NaOH (1 M) and agitated again at 160 rpm. After 20 minutes at pH 6.8, the slurry was decanted with a centrifuge decanter at 4600 g (Z23, Flottweg). In the following examples, the insoluble fraction from decantation was used for napin extraction and was called "wetcake".

TABLE 1

| Starting Cold Press Rapeseed Meal Composition | |
|---|---|
| DM content | 91.7% |
| Proteins/DM | 34.2% |
| Lipids/DM | 21.7% |

The wet cake (32% of dry matter content) was mixed again with water at room temperature (1:3.5 wet-cake:water ratio) under 160 rpm agitation during 15 minutes. The suspension was decanted with a centrifuge decanter at 4600 g (Z23, Flottweg). The liquid phase was clarified by a disc stack separator at 17000 g (Easy Scale, GEA). The solid phases of the second decantation called D2 (25% of the suspension) and sludge from disk stack clarification called C2 (7% of decanted extract) constitute the starting material for Napin Isolate Process described in example 1 to 3. Composition of the starting materials D2 and C2 is given in Table 2.

TABLE 2

|  | D2 | C2 |
|---|---|---|
| DM content | 27% | 7% |
| Protein content | 7% | 3% |
| Phytic acid/proteins | 24.3% | 20.6% |

Example 1: Lab Scale Examples and Comparative Examples for Phytic Acid Removal

A mass of 120 g of lyophilized wet cake D2 was mixed in 1.6 L of water. The pH was adjusted to a value of 2 with chlorhydric acid HCl at a concentration of 1 M. The final solid:liquid ratio was 1:7. pH was maintained at 2 for 30 minutes. Then, a centrifugation step (Thermoscientific Lynx 6000 centrifuge) followed by a filtration step (Whatman filter no 1) took place.

The next step consisted in adjusting the pH, the ionic strength, and/or adding phytase and/or heating at 55° C. pH adjustment was made using sodium hydroxide NaOH 1 M. The ionic strength was obtained by adding NaCl to the required concentration. The phytase used was the phytase described in the following examples. Selected conditions are shown in Table 3. The aqueous extract was maintained in the chosen conditions during 30 minutes or 60 minutes if phytase or heating was applied.

A second centrifugation step allowed the removal of insoluble particles formed during the adjustment step. Then, the pre-purified extract was purified using an ultrafiltration system (GE Healthcare Akta Flux 6, 3 kDa cutoff PS membrane—4500 cm$^2$—hollow fiber). Three diavolumes were carried out maintaining the pH and the ionic strength of the extract followed by 3 diavolumes in ultrapure water. The final retentate was lyophilized and characterized, Table 3.

TABLE 3

| | | Selected conditions | | | | Albumin characterization | | | |
|---|---|---|---|---|---|---|---|---|---|
| No | pH | Ionic strength* | Heating | Phytase | Purity as is | Estimated purity (no salt) | Napin content (% protein) | Phytic acid/ Protein | Solubility at pH 5 |
| 1 | 2 | 0M | No | No | 65% | / | 91.2 | 5.1% | 25% |
| 2 | 2 | 0.5M | No | No | 47% | 71% | 95.5 | 1.4% | 94% |
| 3 | 4.5 | 0M | No | No | 69% | / | 91.2 | 5.6% | 14% |
| 4 | 4.5 | 0.5M | No | No | 49% | 81% | 96.1 | 1.8% | 92% |
| 5 | 4.5 | 0M | Yes | No | 92% | / | 96.5 | 3.2% | 86% |
| 6 | 4.5 | 0M | Yes | Yes | 99.8 | / | 96.9 | 1.0% | 100% |
| 7 | 2 | 0.5M | Yes | No | 72% | >100% | 96.7 | 1.0% | 96% |

*= to added [NaOH]

As can be seen from these examples:
The comparison of selected conditions 1 and 2 shows that an ionic strength of 0.5 M allows the decrease of phytic acid in albumins and the increase of albumin solubility at pH 5
The comparison of selected conditions 1 and 3, and 2 and 4, shows that adjustment of pH has no influence on phytic acid content or purity
The comparison of selected conditions 3 and 5 show that heating at 55° C. allows a strong increase of purity of albumins with a slight decrease of phytic acid content and an increase in solubility at pH 5
The comparison of selected conditions 5 and 6 show that the addition of phytase with heating at 55° C. allows a strong increase of purity of albumins with a strong decrease of phytic acid content and a good solubility at pH 5
The comparison of selected conditions 2 and 7 show that an ionic strength of 0.5 M combined with heating allows both a strong increase a strong increase of purity of albumins with a strong decrease of phytic acid content Moreover, for all selected conditions, the observed albumin proportion is higher than 90%. Hence the following process steps are particularly advantageous in order to considerably increase purity and strongly decrease the phytic acid content:
(1) The use of a phytase at 55° C., at pH 4.5 after extraction; or
(2) The use of salt at 0.5 M at 55° C. after extraction.

Example 2: Pilot Scale's Napin Isolate Production Using a Phytase for Phytic Acid Reduction A quantity of 244 kg of wet cake from second decantation step (D2) was mixed with 50 kg of sludge from clarification step (C2). Tap water at ambient temperature was added in a ratio of 1:3 according to wet cake D2. The slurry was agitated at 160 rpm and pH was adjusted at 2 with phosphoric acid (1 M). After 20 minutes at pH 2, the slurry was decanted with a centrifuge decanter (Z23, Flottweg) at 4600 g at room temperature. The decanted liquid phase was reheated to 55° C. with hot water (60° C.). Phytase Maxamyl P (DSM) was added (1% of dry matter of decanted liquid) and the pH was adjusted to 4.3 with NaOH (1 M). After one hour of phytase digestion, the solution was cooled down to 30° C. to form a precipitate. The precipitated solution was clarified at 30° C. (17000 g) (Easyscale, GEA) and the clarified extract was skimmed with 3 phases disk stack skimmer (ASE40, GEA) at 55° C. for partial oil removal.

The skimmed liquid phase (heavy phase) was microfiltered using a MF system (Pall, 0.8 µm cutoff ceramic GP membrane 4.56 m$^2$) at TMP of 1±0.2 bar. The heavy phase was concentrated 11.2 times and the retentate was diafiltered with 4.3 diafiltrations volume with acidic water (adjusted by phosphoric acid at pH 4.3) to keep constant the permeate pH. The total microfiltration and diafiltration permeates were pooled and ultrafiltered with a UF system (Koch, 5 kDa cutoff PES membrane 32 m$^2$) at TMP of 1±0.2 bar. The MF permeate was concentrated 6.6 times and the UF retentate was diafiltered with 7 diavolumes with water at 55° C. During diafiltration, the pH of the retentate was not controlled and increased from 4.3 to 7.3. The final retentate after ultrafiltration/diafiltration steps was concentrated using a second smaller UF skid (Koch, 5 kDa cutoff PES membrane 4.3 m$^2$) at 55° C. and TMP of 1±0.2 bar. The retentate was concentrated 5.2 times and diafiltered with 2.4 diavolumes with water at 55° C.

The retentate from the second smaller skid UF was freeze dried (Delta2, 24 LSC, Christ). A total of 2170 g of powder were obtained after freeze-drying. The color of the obtained powder was light brown (FIG. 1). This dark color is due to the increase of pH at the diafiltration step. The control of pH during diafiltration will be improved in examples 2, 3, 4.

The proximate composition of the powder is shown in Table 4.

TABLE 4

| | NAPIN Isolate |
|---|---|
| Protein (Nx6.25)/DM (%) | 103 |
| Napin content/Protein | 97% |
| Lipids/DM (%) | 0.5 |
| Ash/DM (%) | 0.9 |
| Polyphenols/DM (%) | 1.4 |
| Phytic Acid (g/100 g proteins) - measured as described below | 2 |
| Histidine (g/100 g proteins) | 4.1 (FAO: 1.5) |
| Isoleucine (g/100 g proteins) | 2.9 (FAO: 3) |
| Leucine (g/100 g proteins) | 6.8 (FAO: 5.9) |
| Lysine (g/100 g proteins) | 8.4 (FAO: 4.5) |
| Methionine + Cysteine (g/100 g proteins) | 7.9 (FAO: 2.2) |
| Phenylalanine + Tyrosine (g/100 g proteins) | 4.5 (FAO: 3.8) |
| Threonine (g/100 g proteins) | 3.3 (FAO: 2.3) |

TABLE 4-continued

| | NAPIN Isolate |
|---|---|
| Tryptophan (g/100 g proteins) | 1.3 (FAO: 0.6) |
| Valine (g/100 g proteins) | 4.5 (FAO: 3.9) |

The process at pilot scale allowed reaching a purity >100% with a phytic acid content at 2% on proteins and a very high solubility (92-95%), whatever the pH, with a well-balanced amino-acid profile. The usual nitrogen to protein conversion factor is 6.25 (N×6.25). But this factor depends on the amino acid composition and therefore depends on the source of protein. For rapeseed, the more accurate conversion factor is between 5.2 and 5.7. But the commercial way to express the protein content remains to use the 6.25 factor (as it is used in the Novel Food for rapeseed isolate—2014) and this is the factor used to determine protein content.

Example 3: Lab Scale's Napin Isolate Production Using a Phytase for Phytic Acid Reduction For this example, the same starting material as in example 1 was used. A quantity of 1.5 kg of wet cake from D2 was mixed with 418 g of sludge from C2. Water at ambient temperature was added in ratio of 1:3 according to wet cake D2. The slurry was agitated at 160 rpm in a 1 L Erlenmeyer and pH was adjusted to 2 with phosphoric acid (2 M). After 30 minutes at pH 2, the slurry was centrifuged under 15000 g during 30 minutes (Thermoscientific Lynx 6000 centrifuge). The supernatant was filtered using a Whatman filter and the filtrate was centrifuged again at 15000 g during 15 minutes. The supernatant from the second centrifugation was heated to 55° C. The pH of the heated liquid was readjusted to 4.5 with NaOH (2 M). Phytase Maxamyl P was added (1% of the total amount of wet cake D2 and sludges C2). The slurry was agitated at 160 rpm in a 1 L Erlenmeyer. After one hour of phytase digestion, the solution was cooled down to 30° C. and a precipitate was observed. The precipitated solution was centrifuged under 15000 g during 15 minutes and the supernatant was filtered again using a Whatman filter.

The filtrate after phytase digestion was ultrafiltered with UF system (GE Healthcare Akta Flux 6, 3 kDa cutoff PS membrane—4500 cm$^2$—hollow fiber). The feed flux is set to 1.5 L/min and the TMP to 1.5 bar. The liquid was concentrated 13.5 times and the UF retentate was diafiltered with 7 diavolumes with water.

The final retentate after diafiltration was freeze dried and 19.7 g of powder were obtained.

TABLE 5

| Protein/DM | Napin content/Protein | Phytic Acid/Protein |
|---|---|---|
| 99% | 99% | 2.0% |

As shown in Table 5, the purity (% of proteins on dry matter) of the powder was high (99%) and the phytic acid content on proteins was low (2.0%). The solubility of the powder was higher than 99%.

The color of the freeze dried napin was very light (FIG. 1).

Example 4: Pilot Scale of Napin Isolate Production with Hexane-Extracted Rapeseed Meal without Phytase and with Salt for Phytic Acid Reduction In this example a defatted (dehulled) rapeseed meal by hexane extraction was made out from dehulled cold press meals used for napin isolate production. The starting meal composition is given on Table 6.

TABLE 6

| Cold Pressed Rapeseed Meal Composition | |
|---|---|
| DM content | 94.5% (94.45%) |
| Proteins/DM | 35.3% (35.32%) |
| Ash/DM | 7.7% (7.69%) |

The process described below leads to two protein fractions: on the one hand, a cruciferin fraction, obtained by isoelectric precipitation and on the other hand, a napin fraction, obtained by membrane purification. The focus will be on napin fraction production.

A quantity of 111 kg of defatted rapeseed meal was mixed with water in a ratio meal:water of 1:8 at ambient temperature. The slurry was agitated at 160 rpm for 10 minutes and the pH was adjusted to 7 with NaOH (1 M). After 45 minutes of extraction at pH 7, the slurry was decanted with a centrifuge decanter at 4600 g (Z23, Flottweg) at room temperature. The decanted liquid phase was heated to 55° C. and clarified with a disk stack clarifier (EasyScale, GEA) at 17000 g. The pH of the clarified liquid phase was adjusted—under agitation at 160 rmp- to 3.5 by addition of phosphoric acid (1 M) to precipitate the cruciferin fraction. The bulk liquid was clarified again with a disk stack clarifier at 17000 g to separate the precipitate (sludge) from the liquid phase. The sludge phase was rich in cruciferin and the liquid phase was rich in napin (C2). The sludge phase was washed by dilution in hot water (55° C.) at pH 3.5 before being clarified again to produce washed sludges containing the cruciferin fraction and a diluted liquid phase (C3).

The C2 and C3 liquid phases constitutes the starting material for the napin process. Clarified liquid phases (C2 and C3) were pooled and microfiltered using a MF system (Pall, 0.1 μm cutoff ceramic GP membrane 6.65 m$^2$) at TMP of 1±0.2 bar. The liquid was concentrated 9.6 times under controlled pH at 3.5. The microfiltration permeate was ultrafiltered with a first UF system (Koch, 5 kDa cutoff PES membrane 32 m$^2$) at TMP of 1±0.2 bar. The MF permeate was concentrated 6.2 times and the UF retentate was diafiltered with 4 diafiltration volumes with water at 55° C.

The ultrafiltered retentate was stored over night at 4° C. and pasteurized (Actini) the day after with a continuous tubular pasteurizer at 75° C. during 15 seconds. The hot water in the heating tubular section was under 76° C. The pasteurized retentate after ultrafiltration/diafiltration steps was concentrated using a second smaller UF skid (Koch, 5 kDa cutoff PES membrane-4.3 m$^2$) at 20° C. and TMP at 1±0.2 bar. The retentate was concentrated 3.6 times and diafiltered with 2 diafiltration volumes with a 0.1 M NaCl solution following by 2 diavolumes with water at 20° C.

Figure 2:
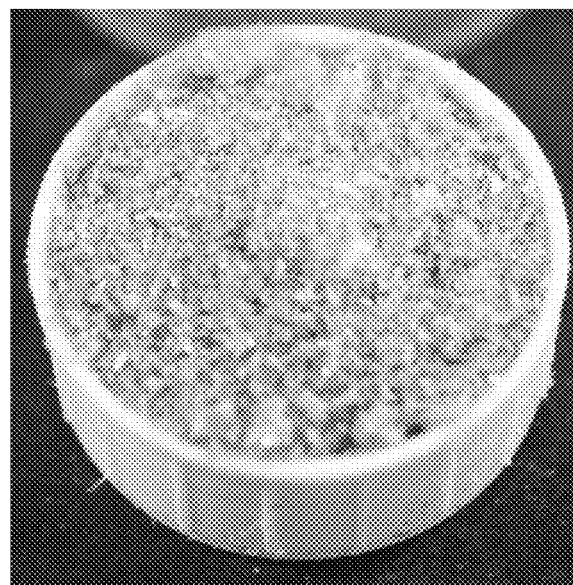
FIG. 2 is a picture of the composition obtained according to Example 4 of the disclosure.

The retentate from the second smaller skid UF was freeze dried (Delta2, 24 LSC, Christ). A total of 970 g of powder was obtained at the end of this step. The color of the powder was light beige as shown in FIG. 2.

TABLE 7

| Protein/DM | Napin content/Protein | Phytic Acid/Protein |
|---|---|---|
| 92% | 92% | 3.6% |

As shown in Table 7, the purity of the powder was high (92%) and composed at 92% of albumins, and the phytic acid content was slightly high. The solubility at pH 5 was 78%.

Example 5: Lab Scale's Napin Isolate Production Using Salt and Heating for Phytic Acid Reduction The starting material would be a dehulled cold press meal.

The objective of this example is to describe an alternative to the phytase step. Salt can be used instead of phytase to significantly reduce the phytic acid content. The acidic extraction is done directly on the cold press meal, without previous extraction carried out at a pH between 6 and 7.8.

The cake is mixed with water to form a slurry and the pH is adjusted to 2 with phosphoric acid 1 M (or HCl 1 M). The slurry is mixed for 30 minutes with a magnetic stirrer in a 1 L Erlenmeyer. The suspension is centrifuged (Thermoscientific Lynx 6000 centrifuge) for 30 minutes at 15000 g and the supernatant is filtered using a Whatman filter. A second centrifugation step to clarify the extract is carried out for 15 minutes at 15000 g and filtered again.

NaCl is added to the clarified extract to reach a concentration of NaCl at 0.5 M. The mixture is heated to 55° C. with a magnetic stirrer in a 1 L Erlenmeyer. These conditions are maintained for 60 minutes. Then, the mixture is cooled down to room temperature. A centrifugation step is carried out for 15 minutes at 15000 g. A solid residue is formed during this step.

The supernatant is filtered and then diafiltered on a UF system (GE Healthcare Akta Flux 6) with a 3 kDa cut-off PS hollow fiber membrane 4800 cm$^2$ from GE Healthcare at room temperature. The feed flux is set to 1.5 L/min and the TMP to 1.5 bar. The first three diavolumes are achieved with salted ultrapure water at a sodium chloride concentration of 0.5 M and pH is maintained at 2 with HCl 1 M. A number of 9 diavolumes are done with ultrapure water only without pH control.

The retentate obtained is freeze-dried.

The product obtained after freeze-drying is put in a bowl and a mortar is used to produce a fine powder which is then analysed.

Figure 3:
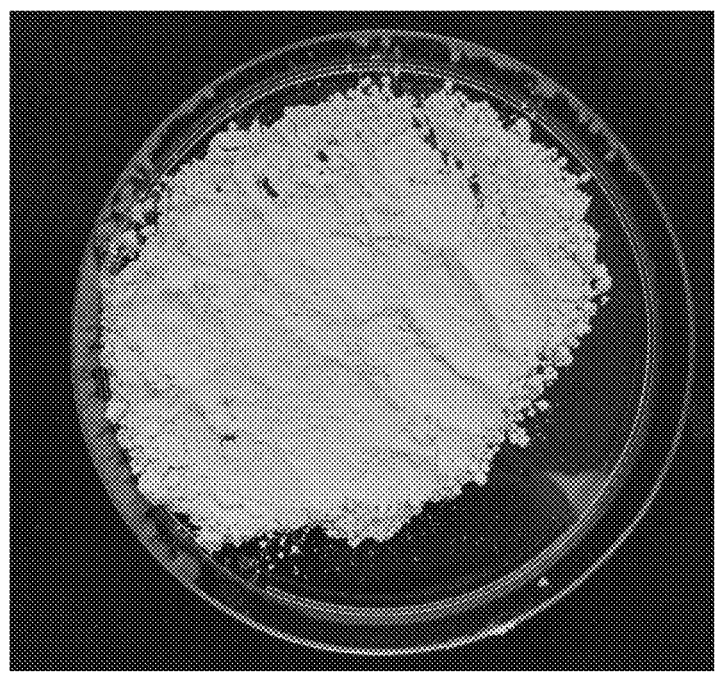
FIG. 3 is a picture of the composition obtained according to Example 5 of the disclosure.

As shown in Table 8, the final powder is characterized by a purity measured as higher than 100% (% proteins/dry matter) and a proportion of at least 94% (possibly 96.7%) of napins with a low phytic acid content: 2.7% on proteins. The solubility at pH 5 is also high with 97%. The color of the powder was very light as shown in FIG. 3.

TABLE 8

| Protein/DM | Napin content/ Protein | Phytic Acid/ Protein | Solubility at pH 5 |
| --- | --- | --- | --- |
| >100% | 94% | 2.7% | 97% |

Comparative Example 1: Lab Scale's Napin Isolate Production According to Cheung et al. (2015), Cf. Supra The starting material was a dehulled cold press meal, no hexane was used.

The process was applied as described by Cheung et al. 180 g of meal was mixed with 1.8 L of water and 0.75% (w/V) of sodium chloride. The pH was adjusted to a value of 3 with hydrochloric acid at a concentration of 1 M. These conditions were maintained 90 minutes. The suspension is centrifuged (Thermoscientific Lynx 6000 centrifuge) for 20 minutes at 4° C. and at 17500 g and the supernatant is filtered using a Whatman filter.

An isoelectric precipitation is carried out by adjusting the pH between 6.8 and 7 with 1 M sodium hydroxide. These conditions are maintained 20 minutes. The suspension is centrifuged (Thermoscientific Lynx 6000 centrifuge) for 20 minutes at 4° C. and at 17500 g and the supernatant is filtered using a Whatman filter.

The obtained extract is concentrated and diafiltered on a UF system (GE Healthcare Akta Flux 6) with a 5 kDa cut-off PS hollow fiber membrane 2000 cm$^2$ from GE Healthcare at room temperature. The feed flux is set to 1 L/min and the TMP between 1.5 and 2 bar. A number of 3 diavolumes are done with ultrapure water only without pH control in order to remove salt and polyphenols.

The retentate obtained is freeze-dried.

The product obtained after freeze-drying is put in a bowl and a mortar is used to produce a fine powder which is then analysed.

As shown in Table 9, the final powder is characterized by a purity measured as 68% (% proteins/dry matter) and a proportion of 94% of napins with a phytic acid content higher than claimed with 9.3% on proteins. The solubility at pH 5 was high with more than 100%.

TABLE 9

| Protein/DM | Napin content/ Protein | Phytic Acid/ Protein | Solubility at pH 5 |
| --- | --- | --- | --- |
| 68% | 94% | 9.3% | >100% |

This comparative example shows that the prior art is not adapted to the treatment of, inter alia, cold pressed oilseed meal. This is due, as shown in Example 1, to the use of an insufficient amount of salt or phytase at the proper stage (e.g. diafiltration stage), in particular in order to reduce the phytic acid content in the final product.

Comparative Example 2: Lab Scale's Napin Isolate Production According to Akbari and Wu (2015), Conf. Supra The starting material was a dehulled cold press meal, no hexane was used.

The process was applied as described by Akbari and Wu (Food Science and Technology, 2015).

The first extraction step consists in mixing 150 g of meal with 1.3 L of water. The pH was adjusted to a value of 4 with hydrochloric acid at a concentration of 1 M. These conditions were maintained 120 minutes. The suspension is centrifuged (Thermoscientific Lynx 6000 centrifuge) for 20 minutes at 5° C. and at 15000 g and the supernatant is filtered using a Whatman filter.

A second extraction step was carried out. 1.2 L of water was added to the wet meal and mixed. The pH was adjusted to 12.5 with sodium hydroxide at a concentration of 1 M. The conditions are maintained during 60 minutes. The suspension is centrifuged (Thermoscientific Lynx 6000 centrifuge) for 20 minutes at 5° C. and at 15000 g and the supernatant is filtered using a Whatman filter. Then the pH of the extract is adjusted to a value between 4 and 4.5 with hydrochloric acid at a concentration between 0.1 and 1 M. The suspension is centrifuged (Thermoscientific Lynx 6000 centrifuge) for 20 minutes at 5° C. and at 15000 g and the supernatant is filtered using a Whatman filter.

The two extracts are pooled and the pH is adjusted to a value of 4 with hydrochloric acid at a concentration of 1 M.

The obtained extract is concentrated to a FCV value of 10.6 and diafiltered on a UF system (GE Healthcare Akta Flux S) with a 10 kDa cut-off PS hollow fiber membrane 140 cm² from GE Healthcare at room temperature. The feed flux is set to 50 mL/min and the TMP between 1.5 and 2 bar. One diavolume was carried out with ultrapure water. However, the purification was stopped because a precipitate formed.

The retentate obtained is freeze-dried.

The product obtained after freeze-drying is put in a bowl and a mortar is used to produce a fine powder which is then analysed.

As shown in Table 10, the final powder is characterized by a purity measured as 68 (% proteins/dry matter) and a proportion of 80% of napins with a very high phytic acid content with 19.6% on proteins. The solubility at pH 5 was low with 66%.

TABLE 10

| Protein/DM | Napin content/ Protein | Phytic Acid/ Protein | Solubility at pH 5 |
|---|---|---|---|
| 56% | 80% | 19.6% | 66% |

In this comparative example, the process applied was not successful because of a precipitation of the proteins during the diafiltration step. This result can be explained from the difference of raw material used: in the article of Akbari and Wu (2015) a hexane-deoiled meal is used whereas, in this example, the main raw material is a cold-pressed meal. This shows the particular suitability of the process of the invention to extract from cold pressed meals.

Measurement of Phytic Acid

The method to determine the percentage of phytic acid in a protein extract or isolate was adapted from Garcia-Estepa et al. (1999, Food International Research) and was applied directly to solid samples such as napin isolates and meals. For each batch of analysis, a blank measurement is carried out with all the reactants excepting the sample to be measured.

1. Extraction

Weigh between 250 and 500 mg of sample in a 25-mL beaker.
Record the exact mass.
Add 20 mL of a solution of HCl 0.4 M+10% $Na_2SO_4$.
Stir for at least 2 h at room temperature.
Centrifuge the suspension for 30 minutes at 10000 g.
Filter the supernatant.

2. Reaction

In a 15 mL centrifuge tube, mix the following solutions:
2.5 mL of the filtered supernatant
2.5 mL of a $FeCl_3$ solution at a concentration of 20 mM
2.5 mL of a HCl 0.4 M+10% $Na_2SO_4$ solution
2.5 mL of sulfosalicylic acid at a concentration of 20% (masse/volume)
Stir, (the mixture should be of a purplish/burgundy color).
The centrifuge tubes are plunged in a 100° C. water bath for 15 to 20 minutes. During this step a precipitate is formed between sulfosalicylic acid, $Fe^{3+}$ ions and phytic acid.
Allow the samples to cool down at room temperature.
Centrifuge the samples for 30 minutes at 10000 g.

3. Recovery of $Fe^{3+}$ ions

The following steps are useful to recover the maximum free ions $Fe^{3+}$.
* The supernatant is filtered on a 0.22 µm filter in a 25 mL volumetric flask.
* A volume of 4 mL of distilled water is added to the tubes containing the precipitates.
* The tubes are stirred vigorously to put the precipitate in suspension. A vortex can be used.
* The samples are centrifuged for 10 minutes at 10000 g.

The above steps with an asterisk "*" are repeated in the same order three times for each samples. Water is added to obtain a 25 mL solution for each sample.

4. Dosage of Free Ions $Fe^{3+}$

For each sample, 10 mL of the previous solution is taken into a 25 mL beaker. 10 mL of water is added.
The pH of each solution is adjusted to 2.5±0.5 by addition of glycine (provided by Sigma Aldrich with a purity of at least 99%).
The solution is then heated in a water bath to a temperature ranging from 70 to 80° C.
The dosage is done directly after the water bath, by addition of a 2 mM of Ethylene diamine tetra acetic acid (EDTA) solution placed in a burette beforehand.
The equivalent volume is reached when the solution changes color from a burgundy color to yellow-green.
The equivalent volume is recorded as precisely as possible.

Calculations

The EDTA dosage allows the quantification of free $Fe^{3+}$ ions in the medium, that is to say, the ions that are not involved in the precipitate with phytic acid.

$$n(Fe^{3+})_{free} = V_{eq} * [EDTA] * 2.5$$

With [EDTA] the concentration in mmol/L, $V_{eq}$ the equivalent volume equivalent in L and 2.5 corresponds to the 10 mL taken from the 25 mL volumetric flask (step 4).

The amount of total $Fe^{3+}$ introduced in the medium is obtained with the dosage of a blank, that is to say, following all the steps but with no sample. The following formula gives the amount of $Fe^{3+}$ in the precipitate.

$$n(Fe^{3+})_{précipitate} = n(Fe^{3+})_{total} - n(Fe^{3+})_{free}$$

This formula can also be written as:

$$n(Fe^{3+})_{précipitate} = n(Fe^{3+})_{blank} - n(Fe^{3+})_{free\ in\ the\ sample}$$

In the literature, it is usually admitted that 6 phosphorus bind to 4 ions $Fe^{3+}$.

$$\frac{n(Phosphorus)}{n(Fe^{3+})} = \frac{6}{4}$$

However, it is supposed that one molecule of phytic acid contains 6 phosphorus.

$$n(Phytic\ Acid) = \frac{n(Phosphorus)}{6}$$

The combination of the last two formulas is:

$$n(Phytic\ Acid)_{precipitate} = \frac{n(Fe^{3+})_{precipitate}}{4}$$

As 2.5 mL were taken from the initial volume of 20 mL (extraction step 1), the molar concentration of phytic acid in the extract is 8 times the concentration of $Fe^{3+}$ ions in the precipitate.

$$n(\text{Phytic Acid})_{extract} = 8 * n(\text{Phytic Acid})_{precipitate}$$

The mass of phytic acid in the extract is:

$$m(\text{Phytic Acid})_{extract} = n(\text{Phytic Acid}) * M(\text{Phytic Acid})$$

M (Phytic Acid) corresponds to the molecular weight of phytic acid, which is equal to 660 g/mol under the IP6 form.

The phytic acid content is usually expressed in mg/g of protein or in mg/g of dry matter corresponding to:

$$\text{Phytic acid content in mg/g of protein} = \frac{m(\text{Phytic Acid})_{extract}}{m(\text{Protein})_{extract}}$$

$$\text{Phytic acid content in mg/g of dry matter} = \frac{m(\text{Phytic Acid})_{extract}}{m(\text{Dry matter})_{extract}}$$

Kjeldahl Method Used for Protein Content Determination

The Kjeldahl method is used for the determination of the protein content in samples under liquid form to assess the solubility of isolates or under solid form to determine the protein content in a sample and is described NF EN ISO 5983-2 Oct. 2009.

1. Preparation of an Isolate Sample Powder 250 mg of the powder is weighted in a 25 mL beaker; the exact mass is recorded.

20 mL of water is added to the powder and the slurry is maintained under agitation at room temperature for 30 minutes.

The solution is then transferred into a 25 mL volumetric flask and water is added to obtain a 25 mL solution.

A 1 mL sample is taken into a Kjeldahl flask.

2. Preparation of a Solid Sample (Meal)

Weigh between 20 and 40 mg of meal in a Kjeldahl Weighing Boat N-free provided by Buchi. Record the exact weight.

Put the boat and the sample in a Kjeldahl flask.

3. General Procedure

In the Kjeldahl flask, introduce 4 mL sulfuric acid at 96% and approximately 0.2 g of catalyst Cu—Se from AppliChem (Gatersleben, Germany).

As control, at least one flask is prepared with no sample but with sulfuric acid and catalyst.

Then, the mineralization step is carried out in several steps in a Büchi SpeedDigester K-439 (Rungis, France):

Preheating to 150° C.

Heating for 15 minutes at 150° C.

Heating for 90 minutes at 450° C.

These steps are done to decompose organic substances: in particular, nitrogen is reduced as $NH_4^+$.

The samples are allowed to cool down for 30 minutes.

The next step is the distillation: sodium hydroxide 32% is added to the sample to convert nitrogen to its $NH_3$ form which is distilled, then converted back to $NH_4^+$ with 3% boric acid and then back titrated with 0.01 M HCl and 3% boric acid in a Kjelflex K-360 from Büchi associated with a Titrino Plus 877 from Metrohm (Herisau, Suisse). The equivalent volume is used in the following calculation.

4. Calculation of the Protein Content

Hence, the total nitrogen content (NTK in g/L) is determined according to the following formula:

$$NTK = \frac{(V_{assay} - V_{blank}) * M(N) * C_n(\text{HCl})}{V_{sample}} \quad (1)$$

$V_{assay}$ and $V_{blank}$ are the volumes of HCl at a concentration of $C_n(\text{HCl})$ equal to 0.01 M (in mL) used for the back titration. M(N) represents the molecular mass of nitrogen, which is 14 g/mol, and $V_{sample}$ is the volume of extract used as sample for the analysis. For the meal analysis, $V_{sample}$ is replaced by the mass of meal introduced in the flask (in mg) and the result becomes a rate of nitrogen in %.

The total nitrogen content is then converted into proteins thanks to a coefficient equal to 6.25.

Protein content=NTK*6.25

It is understood by the skilled person that this measure of protein content is proportional to the amount of nitrogen in the sample.

Measure of the Protein Solubility

In order to measure the solubility, the sample is suspended in deionised water at a protein concentration of 1%. The protein content of this solution is measured by the Kjeldahl method above described. 4 aliquots of 25 mL each are prepared and their pH adjusted with NaOH [1 M] or with HCl [1 M] in water to the desired pH. These aliquots are stirred for at least 20 minutes and then centrifugated (15000 g for 10 minutes). The supernatant are analysed using the Kjeldahl method. Solubility is the ratio between the protein content measured in the deionised water suspension and the one measured after pH adjustment and centrifugation.

Measure of Napin Content

Introduction

Napin content on isolates was evaluated by size exclusion high performance liquid chromatography (SE-HPLC). This analytical technique is used to separate and quantify specific proteins. The separation in SE-HPLC is done according to their molecular size by using a gel composed of porous beads as sieving medium. Smaller molecules will be transported by diffusion inside the beads in an accessible volume related to both their molecular size and bead pore diameters while larger ones will only be transported by a convective flow of eluent between the beads. As a consequence, larger molecules will be eluted first and smaller ones later.

SE-HPLC Device & Eluent Preparation

A Biosep-SEC-s2000 300×7.8 mm provided by Phenomenex was used. This column was chosen as, according to the supplier, its separation range is between 1 and 300 kDa, which cover the sizes of the proteins under study. Inside the column, the gel is composed of silica with a particle size of 5 μm and a pore size of 145 Å.

The chromatographic system is a UFLC machine from Shimadzu which is equipped with Photodiode Array (PDA) detector and a column oven set at 35° C. Detection was set to 214 nm and data were processed with the LabSolution software.

Eluent was prepared with 45% acetonitrile provided by Biosolve BV (Valkenswaard, the Netherlands) and 55% Ultra-Pure Water. 0.1% of trifluoroacetic acid (TFA) was added to the mixture. Elution was set with a 0.6 mL/min flow and lasted 30 minutes. The mixture of water and acetonitrile is commonly used to study proteins and their possible aggregates.

Samples Preparation

A solution of 5 g/L of isolate in pure water was prepared by dissolving 125 grs of powder in 25 mL of pure water and maintained under agitation at room temperature for 30 minutes. 10 mL of the solution was filtered on 0.22 μm syringe filter and introduced in vials. A volume of 5 μL sample was injected.

Results

Typical results obtained with SE-HPLC analysis from rapeseed isolate is given in FIG. 4. The first peak corresponds to cruciferin and the second peak to the napin.

The area under the curve (A) of each peak is calculated and thus allows to return to the napin content on the isolate. This calculation is simple as the mass extinction coefficient of both proteins, measured thanks to calibration curves on napin and cruciferin isolates, is the same. Napin content in isolate is given by the following equation (eq.1):

$$\text{Napin content (\%)} = 100 \times \frac{A_{napin}}{A_{napin} \times A_{cruciferin}} \quad \text{(eq 1)}$$

FIG. 4 shows the correlation between the peaks observed by SE-HPLC and SDS-PAGE analysis in reducing conditions. The first peak corresponds to a high molecular weight protein, cruciferins, which is composed six subunits which are in turn composed of two main polypeptides, an α-chain (around 30 kDa) and a β-chain (around 20 kDa), visible on the SDS-PAGE gel.

The second peak is consistent with a low molecular weight protein, napins, which is composed of two main subunits, one small with 4 kDa, the other long with 9 kDa, associated together by a disulfide bond. FIG. 5 is a chromatogram obtained after preparing a solution of 10 g/L of napin isolate. Hence, one main peak is clearly visible at the same retention time as in FIG. 4.

The separated proteins are subunits still associated by their disulfide bridge as the elution conditions allow the dissociation of electrostatic and ionic interaction but not of the disulfide bridges.

It will be understood that these are examples of suggested operating conditions and the composition of the liquid to be separated can necessitate operating at different condition or using separation techniques other than a centrifuge to separate solids from liquids or two immiscible liquid phases.

The invention claimed is:

1. A process for producing a protein isolate from an oilseed meal, said isolate comprising proteins and an amount of 4 wt. % or less of phytic acid, said amount of phytic acid being by weight of proteins in said isolate, said process comprising the following steps:
    a) providing cold-pressed, partially defatted, oilseed meal said oilseed meal being selected from the group consisting of rapeseed, canola, flax, lupine, sunflower, safflower, cotton, mustard and hemp seed meals, and mixtures thereof and said oilseed meal comprising from about 5 wt % to about 20 wt % of oil, by total weight of dry matter of partially defatted meal;
    b) mixing the oilseed meal with a first aqueous solvent to form a slurry at a pH ranging from 6 to 7.8, said slurry having a solid phase;
    c) separating said solid phase from said slurry to obtain a separated solid phase;
    d) mixing said separated solid phase with a second aqueous solvent at a pH ranging from 1 to 3.5, to form a mixture said mixture having a liquid phase;
    e) separating said liquid phase from said mixture formed in the step d) to obtain a separated liquid phase;
    f) f1) mixing the separated liquid phase with a phytase at a temperature and a pH suitable for phytase activity to obtain a mixture having a liquid phase and a solid phase;
    and/or
    f2) mixing the separated liquid phase with a salt, to obtain a resulting liquid composition having a molar concentration of said salt ranging from 0.05 M to 0.5 M, at a temperature ranging from 40° C. to 70° C., to obtain a mixture having a liquid phase and a solid phase;
    g) precipitating a solid phase from the liquid phase of the step f) to obtain a solid precipitate;
    h) separating said solid precipitate from the liquid phase of the step g) said liquid phase comprising a water-rich liquid phase and an oil-rich liquid phase;
    i) separating said water-rich liquid phase from said oil-rich liquid phase,
    j) subjecting said water-rich liquid phase obtained in the step i) to one or several membrane filtration(s) to obtain a protein isolate; and
    k) optionally, drying said protein isolate to obtain a dry protein isolate.

2. The process according to claim 1, wherein the oilseed meal is a cold-press oilseed meal which has been cold-pressed at a temperature of 85° C. or less.

3. The process according to claim 1, wherein said salt is sodium chloride.

4. The process according to claim 1, wherein a ratio of the oilseed meal to the first aqueous solvent ranges from 1:5 to 1:20 (w/w).

5. The process according to claim 1, wherein any one of the steps c), e), h), i) and/or j) is repeated.

6. The process according to claim 1, wherein the step j) comprises the following steps:
    j1) optionally subjecting the water-rich liquid phase obtained in the step i) to at least one microfiltration step and harvesting a permeate,
    j2) subjecting the water-rich liquid phase obtained in the step i) or the permeate of the step j1) to at least one ultrafiltration step, optionally followed by at least one diafiltration step, and harvesting the protein isolate.

7. The process according to claim 1, wherein the steps a) to e), i) and j) are conducted at room temperature.

8. The process according to claim 1, comprising mixing said separated solid phase with a second aqueous solvent at a pH ranging from 2 to 3, to form a mixture said mixture having a liquid phase.

9. The process according to claim 1, wherein said precipitating a solid phase from the liquid phase of the step g) comprises a cooling down step of the mixture to a temperature of 30° C. or less.

10. The process according to claim 1, wherein the oilseed meal is selected from the group consisting of rapeseed, canola and sunflower seed meals and mixtures thereof.

11. The process according to claim 1, wherein the oilseed meal is a cold-press oilseed meal which has been cold-pressed at a temperature of 60° C. or less.

12. The process according to claim 1, wherein a ratio of the oilseed meal to the first aqueous solvent ranges from 1:6 to 1:10 (w/w).

13. The process according to claim 1, wherein oilseeds are first at least partially dehulled before being transformed into said oilseed meal.

14. The process according to claim 1, wherein the step f1) and/or the step f2) is carried out at 55° C.±2° C.

15. The process according to claim 1, wherein no hexane is used to extract oil from the oilseed meal.

16. A process for producing a protein isolate from an oilseed meal, said isolate comprising proteins and an amount of 3 wt. % or less of phytic acid, said amount of phytic acid being by weight of proteins in said isolate, said process comprising the following steps:
   i. providing cold-pressed, partially defatted, oilseed meal said oilseed meal being selected from the group consisting of rapeseed, canola, flax, lupine, sunflower, safflower, cotton, mustard and hemp seed meals, and mixtures thereof and said oilseed meal comprising from about 5 wt % to about 20 wt % of oil, by total weight of dry matter of partially defatted meal;
   ii. mixing said oilseed meal with an aqueous solvent at a pH ranging from 1 to 3.5 to form a mixture said mixture having a liquid phase;
   iii. separating said liquid phase from said mixture formed in the step ii) to obtain a separated liquid phase;
   iv. mixing the separated liquid phase with a phytase at a temperature and a pH suitable for phytase activity to obtain a mixture having a liquid phase and a solid phase; and/or
   v. precipitating a solid phase from the liquid phase of the step iv) by a cooling down step of the mixture to a temperature of 30° C. or less to obtain a solid precipitate;
   vi. separating said solid precipitate from the liquid phase of the step v), said liquid phase comprising a water-rich liquid phase and an oil-rich liquid phase;
   vii. separating said water-rich liquid phase from said oil-rich liquid phase,
   viii. subjecting said water-rich liquid phase obtained in the step vii) to one or several membrane filtration(s) to obtain a protein isolate; and
   ix. optionally, drying said protein isolate to obtain a dry protein isolate.

17. The process according to claim 16, comprising mixing said oilseed meal with an aqueous solvent at a pH ranging from 2 to 3, to form a mixture said mixture having a liquid phase.

18. The process according to claim 16, wherein oilseeds are first at least partially dehulled before being transformed into said oilseed meal.

19. The process according to claim 16, wherein the step f1) and/or the step f2) is carried out at 55° C.±2° C.

20. The process according to claim 16, wherein no hexane is used to extract oil from the oilseed meal.

21. A process for producing a protein isolate from an oilseed meal, said isolate comprising proteins and an amount of 3 wt. % or less of phytic acid, said amount of phytic acid being by weight of proteins in said isolate, said process comprising the following steps:
   A. providing cold-pressed, partially defatted, oilseed meal said oilseed meal being selected from the group consisting of rapeseed, canola, flax, lupine, sunflower, safflower, cotton, mustard and hemp seed meals, and mixtures thereof, and said oilseed meal comprising from about 5 wt % to about 20 wt % of oil, by total weight of dry matter of partially defatted meal;
   B. mixing the oilseed meal with a first aqueous solvent to form a slurry at a pH ranging from 6 to 7.8, said slurry having a liquid phase;
   C. separating said liquid phase from said slurry to obtain a separated liquid phase,
   D. adjusting the pH of said separated liquid phase at a pH ranging from 2 to 4, to form a mixture said mixture having a liquid phase and a solid precipitate;
   E. separating said liquid phase from said solid precipitate;
   F. subjecting the liquid phase obtained in the step E. to a microfiltration step, and recovering a permeate;
   G. subjecting said permeate recovered in the step F. to an ultrafiltration step which is followed by at least one diafiltration step carried out with an aqueous solution of a salt to obtain said protein isolate; and
   H. optionally, drying said protein isolate to obtain a dry protein isolate.

22. The process according to claim 21, comprising adjusting the pH of said separated liquid phase at a pH ranging from 3 to 3.8, to form a mixture said mixture having a liquid phase and a solid precipitate.

23. The process according to claim 21, wherein oilseeds are first at least partially dehulled before being transformed into said oilseed meal.

24. The process according to claim 21, wherein the step f1) and/or the step f2) is carried out at 55° C.±2° C.

25. The process according to claim 21, wherein no hexane is used to extract oil from the oilseed meal.

* * * * *